United States Patent
Cohen et al.

(10) Patent No.: US 10,957,057 B2
(45) Date of Patent: Mar. 23, 2021

(54) POST-MAPPING AUTOMATIC IDENTIFICATION OF PULMONARY VEINS

(71) Applicant: Biosense Webster (Israel) Ltd., Yokneam (IL)

(72) Inventors: Assaf Cohen, Kiryat Bialik (IL); Itai Doron, Katsir (IL); Fady Massarwi, Baka Al Gharbiyya (IL); Ido Ilan, Yoqneam (IL); Akram Zoabi, Kfar Masser (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 245 days.

(21) Appl. No.: 16/109,018

(22) Filed: Aug. 22, 2018

(65) Prior Publication Data

US 2020/0065983 A1  Feb. 27, 2020

(51) Int. Cl.
*G06K 9/00* (2006.01)
*G06T 7/33* (2017.01)
*G06T 7/11* (2017.01)
*A61B 5/283* (2021.01)
*G06T 17/00* (2006.01)

(52) U.S. Cl.
CPC ............... *G06T 7/33* (2017.01); *A61B 5/283* (2021.01); *G06T 7/11* (2017.01); *G06T 17/00* (2013.01); *G06T 2207/30048* (2013.01)

(58) Field of Classification Search
CPC ... G06T 7/33; G06T 7/11; G06T 17/00; G06T 2207/30048; A61B 5/042
See application file for complete search history.

(56) References Cited

U.S. PATENT DOCUMENTS

| | | | | |
|---|---|---|---|---|
| 5,797,844 | A * | 8/1998 | Yoshioka | G01S 7/52036 600/442 |
| 7,110,583 | B2 * | 9/2006 | Yamauchi | G06T 7/12 382/128 |
| 10,575,823 | B2 * | 3/2020 | Okazaki | A61B 8/488 |
| 10,635,930 | B2 * | 4/2020 | Geiger | G06T 7/73 |
| 2007/0276225 | A1 | 11/2007 | Kaufman et al. | |
| 2008/0085042 | A1 | 4/2008 | Trofimov et al. | |
| 2011/0160569 | A1 * | 6/2011 | Cohen | G06T 7/246 600/424 |
| 2012/0172724 | A1 | 7/2012 | Hill et al. | |
| 2018/0315188 | A1 * | 11/2018 | Tegzes | G06T 7/11 |

OTHER PUBLICATIONS

Gao, Zhiyun, "Novel multi-scale topo-morphologic approaches to pulmonary medical image processing", The University of Iowa's Institutional Repository, Iowa Research Online, Theses and Dissertations, Dec. 2010.
European Search Report for corresponding EPA No. 19192909.0 dated Dec. 2, 2019.
Matthias Hoffman et al., "Automatic Detection of Ostia in the Left Atrium", Informatik Aktuell, Jan. 1, 2016, pp. 224-229.
Liu Bo et al., "Stable and real-time hand gesture recognition based on RGB-D data" Visual Communications and Image Processing, Jan. 20, 2004, pp. 904501-90450L.

* cited by examiner

*Primary Examiner* — Shefali D Goradia

(57) ABSTRACT

A method includes calculating a center-of-mass of a volume of an organ of a patient in a computerized anatomical map of the volume. A location is found on the anatomical map, on a surface of the volume, that is farthest from the center-of-mass. The location is identified as a known anatomical opening of the organ.

12 Claims, 2 Drawing Sheets

POST-MAPPING AUTOMATIC IDENTIFICATION OF PULMONARY VEINS

FIELD OF THE INVENTION

The present invention relates generally to cardiac mapping, and particularly to analyzing anatomical cardiac maps.

BACKGROUND OF THE INVENTION

Some clinical procedures employ techniques for obtaining an anatomical map of an organ such as a cardiac chamber. For example, U.S. Patent Application Publication 2008/0085042 describes a method for imaging, which includes receiving a first three-dimensional (3D) image of a vicinity of an organ within a body of a subject and creating a geometrical model of a tubular structure in the first 3D image in the vicinity of the organ. An invasive probe is inserted into the organ, and a second 3D image containing the organ is captured using the invasive probe. One or more points are located on a surface of the tubular structure using the invasive probe, and the second 3D image is registered with the first 3D image by matching the one or more points to the geometrical model.

As another example, U.S. Patent Application Publication 2012/0172724 describes an intracardiac imaging system that is configured to display electrode visualization elements within an intracardiac echocardiography image. The system further allows cross sections of tissue structures embodied in intracardiac echocardiography images to be modeled within a visualization, navigation, or mapping system when automatically segmented to generate shell elements for modifying the modeled tissue structures.

U.S. Patent Application Publication 2007/0276225 describes methods for generating a three-dimensional visualization image of an object, such as an internal organ, using volume visualization techniques. The techniques include a multi-scan imaging method; a multi-resolution imaging method; and a method for generating a skeleton of a complex three-dimensional object. The applications include virtual cystoscopy, virtual laryngoscopy, virtual angiography, among others.

SUMMARY OF THE INVENTION

An embodiment of the present invention provides a method including calculating a center-of-mass of a volume of an organ of a patient in a computerized anatomical map of the volume. A location is found on the anatomical map, on a surface of the volume, that is farthest from the center-of-mass. The location is identified as a known anatomical opening of the organ.

In some embodiments, the method includes calculating paths from the center-of-mass to multiple locations on the surface of the volume, and finding a longest path among the multiple paths.

In some embodiments, the method includes including multiple locations on the surface of the volume that are within a predefined distance from the found location as being part of the opening.

In an embodiment, the method includes dividing the surface of the volume into a given number of pixels, and calculating a shortest path to each pixel.

In another embodiment, the method further includes finding on the anatomical map one or more next-farthest locations on a surface of the volume, which are farthest from the center-of-mass after excluding the identified opening, and farthest from the identified opening among the one or more next-farthest locations, and identifying the next-farthest locations as one or more additional openings.

In some embodiments, the method includes iteratively finding each of the next-farthest locations by selecting each next-farthest location based on being farthest, among the one or more next-farthest locations, from the identified openings, until finding a pre-set number of locations.

In some embodiments, the volume includes a cardiac chamber.

In an embodiment, the method further includes presenting the found location to a user.

There is additionally provided, in accordance with an embodiment of the present invention, a system including a memory and a processor. The memory is configured to store a computerized anatomical map of a volume of an organ of a patient. The processor is configured to calculate a center-of-mass of a volume of an organ of a patient in the anatomical map, and to find on the anatomical map a location on a surface of the volume that is farthest from the center-of-mass. The processor is further configured to identify the location as a known anatomical opening of the organ.

The present invention will be more fully understood from the following detailed description of the embodiments thereof, taken together with the drawings in which:

BRIEF DESCRIPTION OF THE DRAWINGS

FIG. 1 is a schematic, pictorial illustration of a system for electro-anatomical mapping, in accordance with an embodiment of the present invention;

FIG. 2 is a schematic, pictorial volume rendering of an anatomical map, which exemplifies an automatic identification of candidate openings in a volume, in accordance with an embodiment of the present invention; and FIG. 3 is a flow chart that schematically illustrates a method for identifying openings of pulmonary veins on an anatomical map of a left atrium, in accordance with an embodiment of the present invention.

DETAILED DESCRIPTION OF EMBODIMENTS

Overview

Catheter-based anatomical mapping techniques may produce a map of a cavity (i.e., volume) of an organ. In some cases, the mapping technique is not anatomically aware of anatomical openings in the volume. For example, mapping of a left atrium (LA) of a heart may not denote the openings of the four pulmonary veins (PV). Thus, the identification of features (e.g., openings) in such maps with known anatomical structures may require input from a trained, qualified person, such as a radiologist or a cardiologist, to identify certain anatomical landmarks in the mapped volume that hint at an opening, such as, for example, openings in a map of the LA, based on landmarks of ostia of the PVs.

Embodiments of the present invention that are described herein provide methods for automatically finding and denoting openings in a computerized anatomical map of a cavity of an organ. In some embodiments, a processor receives an anatomically mapped cavity and searches the map for known anatomical openings, so as to make the anatomical map aware of, and denote, these anatomical landmarks of the mapped cavity.

In some embodiments, the processor receives a computerized anatomical map of a volume (i.e., cavity) of an organ and calculates the center of mass of the mapped volume.

Then, the processor finds the farthest point from the center of mass on the map. This point is assumed to be on an opening, and, in the case of a map of an LA, such a point is assumed to be located at an ostium of a PV. The processor then includes, in the opening, all points that fall within a predefined distance from the farthest point, all of which are assumed to be part of the found PV. Next, the processor denotes all locations on the map as part of the found candidate PV.

Once the processor has found a first opening (e.g., an ostium of a PV), the processor searches for other "farthest" points in the volume. In some embodiments the processor finds, one by one, "next-farthest" points. A next farthest point is selected based on being next-farthest from the center of mass, and farthest among all other candidate points from the already found candidate opening. The later condition is set so as to ensure the process does not define in error candidates that are too close to each other than possible. In particular, a next farthest is not included in the first found candidate opening (e.g., locations on a map beyond a predefined distance from the farthest point). The processor iterates the search, wherein a next farthest point is selected based on being next-farthest from the center of mass, and farthest among all other candidate points from the already found candidate openings, until a pre-set number of structures (e.g., openings) is found.

In an embodiment, the processor finds at least five candidate openings in an LA map: four PVs and a mitral valve. The pre-set number of candidate openings for search may be set to six, for example, in order to ensure that all candidate openings are captured. Further analysis is then used to identify the five farthest locations found, with one or more commonly known anatomical openings of the LA. For example, such analysis may be done by correlating candidate openings with ostia of PVs that are marked on a non-patient specific anatomical model of the LA.

In some embodiments, the processor finds the candidate openings in the anatomical map by splitting the surface of the mapped volume into pixels, calculating a path to each pixel, comparing path-lengths, ranking paths according to their lengths, and denoting locations with the longest paths and their surroundings as candidate openings.

The disclosed technique uses automated post-processing methods to analyze an anatomical map. The technique simplifies the analysis of an anatomical map by easing the diagnostic interpretation work required by a physician. The disclosed technique may thus expedite complicated diagnostic procedures, such as those required in diagnostic catheterizations, and by so doing make the clinical diagnosis and treatment cycle more readily available to patients.

System Description

Figure 1:
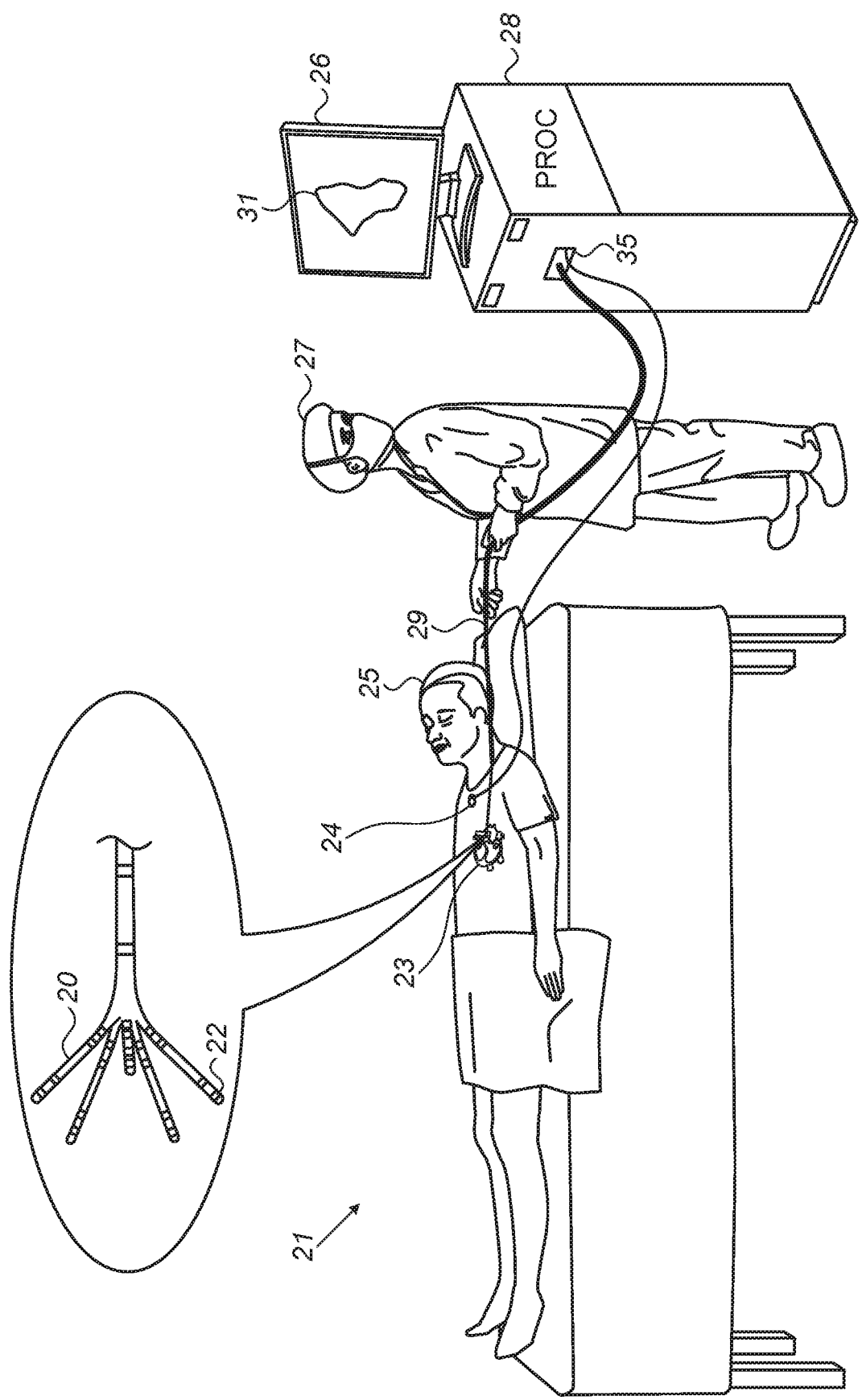

FIG. 1 is a schematic, pictorial illustration of a system for electro-anatomical mapping, in accordance with an embodiment of the present invention. FIG. 1 depicts a physician 27 using an electro-anatomical catheter 29 to perform an electro-anatomical mapping of a heart 23 of a patient 25. Catheter 29 comprises, at its distal end, one or more arms 20, which may be mechanically flexible, each of which is coupled with one or more electrodes 22. During the mapping procedure, electrodes 22 acquire and/or inject signals from and/or to the tissue of heart 23. A processor 28 receives these signals via an electrical interface 35, and uses information contained in these signals to construct an electro-anatomical map 31. During and/or following the procedure, processor 28 may display electro-anatomical map 31 on a display 26.

During the procedure, a tracking system is used to track the respective locations of sensing-electrodes 22, such that each of the signals may be associated with the location at which the signal was acquired. For example, the Active Current Location (ACL) system, made by Biosense-Webster (Irvine Calif.), which is described in U.S. Pat. No. 8,456,182, whose disclosure is incorporated herein by reference, may be used. In the ACL system, a processor estimates the respective locations of the electrodes based on impedances measured between each of the sensing-electrodes 22, and a plurality of surface-electrodes 24, that are coupled to the skin of patient 25. For example, three surface-electrodes 24 may be coupled to the patient's chest, and another three surface-electrodes may be coupled to the patient's back. (For ease of illustration, only one surface-electrode is shown in FIG. 1.) Electric currents are passed between electrodes 22 inside heart 23 of the patient, and surface-electrodes 24. Processor 28 calculates an estimated location of all electrodes 22 within the patient's heart based on the ratios between the resulting current amplitudes measured at surface-electrodes 24 (or between the impedances implied by these amplitudes) and the known positions of electrodes 24 on the patient's body. The processor may thus associate any given impedance signal received from electrodes 22 with the location at which the signal was acquired.

The example illustration shown in FIG. 1 is chosen purely for the sake of conceptual clarity. Other tracking methods can be used, such as ones based on measuring voltage signals, as with the Carto®4 system (produced by Biosense Webster). Other types of sensing catheters, such as the Lasso® Catheter (produced by Biosense Webster) may equivalently be employed. Contact sensors may be fitted at the distal end of electro-anatomical catheter 29. As noted above, other types of electrodes, such as those used for ablation, may be utilized in a similar way, fitted to electrodes 22 for acquiring the needed position data. Thus, an ablation electrode used for collecting position data is regarded, in this case, as a sensing-electrode. In an optional embodiment, processor 28 is further configured to indicate the quality of physical contact between each of the electrodes 22 and an inner surface of the cardiac chamber during measurement.

Processor 28 typically comprises a general-purpose computer with software programmed to carry out the functions described herein. The software may be downloaded to the computer in electronic form, over a network, for example, or it may, alternatively or additionally, be provided and/or stored on non-transitory tangible media, such as magnetic, optical, or electronic memory.

Post Mapping Automatic Identification of
Pulmonary Veins

Figure 2:
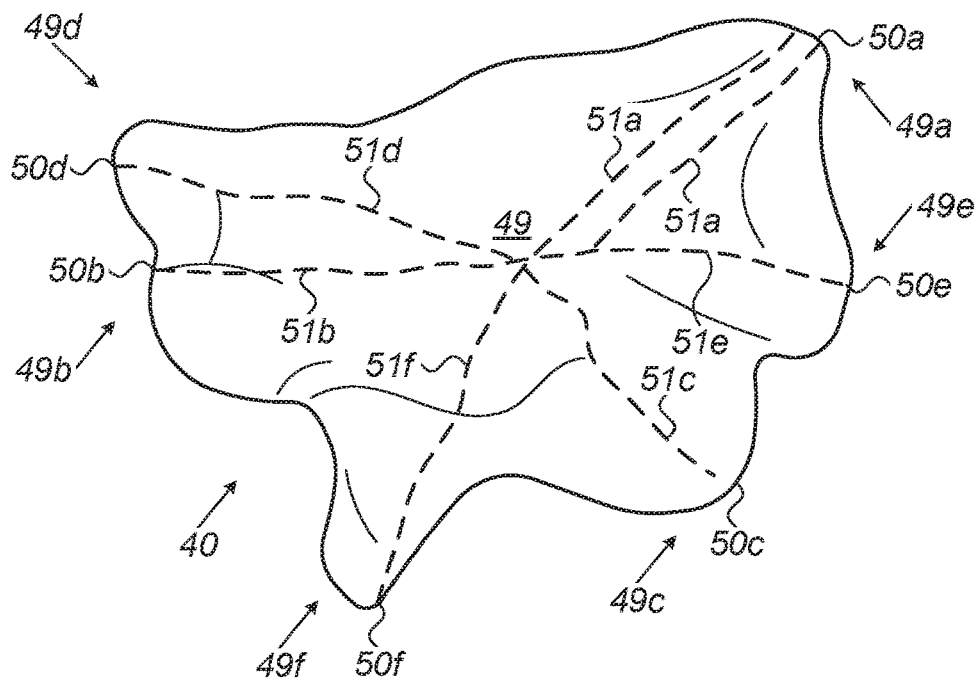

FIG. 2 is a schematic, pictorial volume rendering of an anatomical map, which exemplifies an automatic identification of candidate openings 49a-f in a volume 40 of a patient's left atrium, in accordance with an embodiment of the present invention. As seen, FIG. 2 shows a "water-tight closed mesh" rendering of an anatomical map of a volume. The disclosed post-mapping process, applied, for example, by processor 28, implements a path-length calculation scheme in order to identify openings.

The example provided by FIG. 2 shows resulting paths 51a-f, brought, by way of example, as paths found to be among the longest, calculated by processor 28 on volume 40 of the left atrium, which lead to finding candidate openings 49a-f some of which belong to pulmonary veins. To calculate paths 51a-f, processor 28 first calculates a center of mass location 49 of mapped volume 40. Center of mass location 49 of mapped volume 40 is defined as the average position of all defined points (e.g., voxels on a computerized anatomical map) of mapped volume 40. In general, center of mass location 49 can be found by vector addition of the position vectors pointing each to one of the defined points in mapped volume 40.

Next, the processor applies, on the map, a path-length calculation. For example, processor 28 may divide the map into small sections (e.g., groups of neighboring voxels) in order to ensure that its calculations cover all possible paths with sufficient spatial resolution. In an embodiment, processor 28 divides the surface area of the mapped volume to a given number of pixels and calculates the shortest path from the center of mass to each pixel.

Once the processor has found a first opening 49a (e.g., an ostium of a PV), the processor searches for other "farthest" points in the volume. In some embodiments the processor finds, one by one, "next-farthest" points. A next farthest point is selected based on being next-farthest from the center of mass, and farthest among all other candidate points from the already found candidate opening, for example point 50b is farthest from point 50a among points 50b-f, point 50c is farthest from points 50a-b among points 50c-f, and so on. The later condition is set so as to ensure the process does not define in error candidates that are too close to each other than possible. In particular, a next farthest is not included in the first found candidate opening (e.g., locations on a map beyond a predefined distance from the farthest point). The processor iterates the search, wherein a next farthest point is selected based on being next-farthest from the center of mass, and farthest among all other candidate points from the already found candidate openings, until a pre-set number of structures (e.g., openings) is found.

Resulting paths 51a-f are shown, to which processor subsequently associates six corresponding farthest 28 locations (i.e., points), 50a-f, to be candidate locations of an opening, most probably an ostium of a PV. To define a corresponding candidate opening on a map, all points on map 40 within a predefined distance from a found location are included as part of the candidate opening as seen in location 50a, two paths having very similar path-lengths are found, but still one of the two is the shortest.

Figure 3:
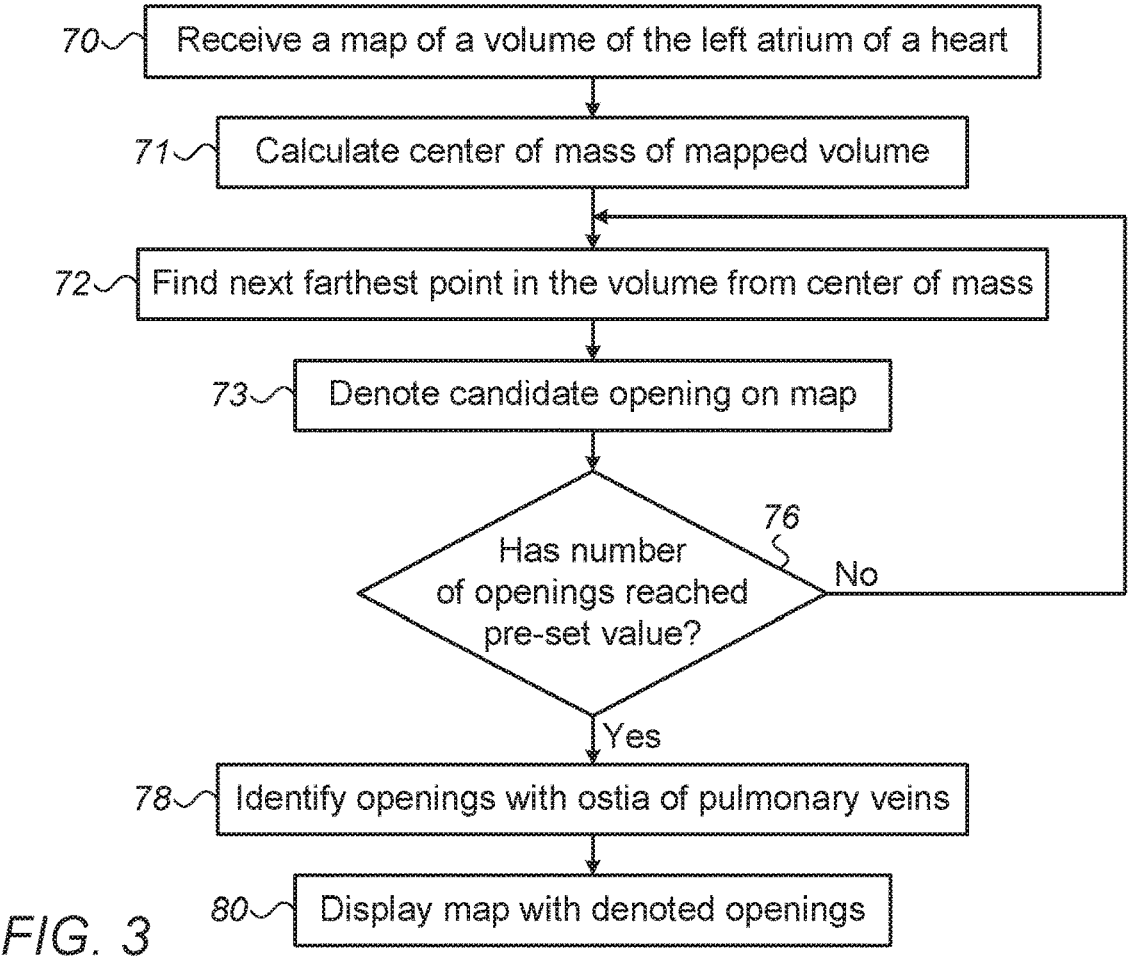

FIG. 3 is a flow chart that schematically illustrates a method for identifying openings of pulmonary veins on an anatomical map of a left atrium, in accordance with an embodiment of the present invention. The procedure begins with processor 28 receiving a map of the LA of a heart 23 of patient 25, such as map 40 computed by system 21, at a mapping step 70.

Next, processor 28 calculates center of mass location 49 of the mapped LA volume, at a calculation step 71. Next, by calculation of paths, processor 28 finds the farthest location in the mapped volume from center of mass location 49 (in the present example, location 49a that has one or more longest path-lengths), at a location finding step 72. Next farthest point is selected (i.e., in step 72) based on being next-farthest from the center of mass and farthest among all other candidate points from the already found candidate opening.

The processor then denotes the farthest location, and all points on the map that are within a predefined distance of the farthest location on the map, as a candidate opening 49a, at an opening denoting step 73.

At a checking step 76, the process checks if a pre-set number of farthest locations has been found. If not, the method loops back to step 72 in which the processor continues the search by finding the next-farthest points (beginning with finding point 50b). In this manner the processor iteratively finds the next-farthest locations. For finding the next-farthest locations on a surface of the volume from center-of-mass 49, the processor excludes the previously-identified openings.

The iterative process of steps 72-76 continues until the pre-set number of candidate openings is reached (i.e., until the processor found the pre-set number of locations). In the present example, purely by way of example, the preset number equals six.

Once the pre-set number of candidate openings have been found, processor 28 identifies one or more of the found locations with one or more commonly known PV ostia of the LA volume, at an opening identifying step 78. The identification may rely, for example, on the commonly known anatomical arrangement of the ostia. Finally, at a displaying step 80, the processor displays the computerized anatomical map with the denoted openings to physician 27 on display 26. Physician 27 may use the displayed map to plan and perform an ablation of an opening, such as ablation of an ostium of a pulmonary vein at the left atrium.

The example flow chart shown in FIG. 3 is chosen purely for the sake of conceptual clarity. In optional embodiments, various additional steps may be performed, for example to automatically register, with medical images, openings that were identified in steps 70-80.

Although the embodiments described herein mainly address identification of known anatomical openings in a mapped volume, such as ostia of pulmonary veins, the methods and systems described herein can also be used in other applications. For example, the disclosed method may be utilized to identify zones in a cavity that have a disproportionate size and/or shape. While disclosed embodiments refer to cardiac applications, the disclosed method may be applied to a mapped volume of a cavity of any organ. For example, the method can be applied to an otolaryngologic map.

It will be appreciated that the embodiments described above are cited by way of example, and that the present invention is not limited to what has been particularly shown and described hereinabove. Rather, the scope of the present invention includes both combinations and sub-combinations of the various features described hereinabove, as well as variations and modifications thereof which would occur to persons skilled in the art upon reading the foregoing description and which are not disclosed in the prior art. Documents incorporated by reference in the present patent application are to be considered an integral part of the application except that to the extent any terms are defined in these incorporated documents in a manner that conflicts with the definitions made explicitly or implicitly in the present specification, only the definitions in the present specification should be considered.

The invention claimed is:

1. A method for finding and denoting anatomical features in an anatomical map, the method comprising:

receiving a map of an organ of a patient generated from data collected utilizing an electro-anatomical catheter positioned in the organ;

calculating a center-of-mass of a volume of the organ of a patient in a computerized anatomical map of the volume;

finding on the anatomical map a location on a surface of the volume that is farthest from the center-of-mass;

finding on the anatomical map one or more next-farthest locations on a surface of the volume, which are farthest from the center-of-mass after excluding the identified opening, and farthest from the identified opening among the one or more next-farthest locations, and identifying the next-farthest locations as one or more additional openings, wherein finding the next-farthest locations comprises iteratively finding each of the next-farthest locations by selecting each next-farthest location based on being farthest, among the one or more next-farthest locations, from the identified openings, until finding a pre-set number of locations; and identifying the location as a known anatomical opening of the organ.

2. The method according to claim 1, wherein finding the location comprises calculating paths from the center-of-mass to multiple locations on the surface of the volume, and finding a longest path among the multiple paths.

3. The method according to claim 2, wherein identifying the location comprises including multiple locations on the surface of the volume that are within a predefined distance from the found location as being part of the opening.

4. The method according to claim 2, wherein calculating the paths comprises dividing the surface of the volume into a given number of pixels, and calculating a shortest path to each pixel.

5. The method according to claim 1, wherein the volume comprises a cardiac chamber.

6. The method according to claim 1, further comprising presenting the found location to a user.

7. A system for finding and denoting anatomical features in an anatomical map, the system comprising:
   an apparatus, including an electro-anatomical catheter, for creating an anatomical map, the electro-anatomical catheter being positioned within the organ to gather data for creating the map;
   a memory, configured to store a computerized anatomical map of a volume of an organ of a patient; and
   a processor, configured to:
      calculate a center-of-mass of a volume of an organ of a patient in the anatomical map;
      find on the anatomical map a location on a surface of the volume that is farthest from the center-of-mass;
      find on the anatomical map one or more next-farthest locations on a surface of the volume, which are farthest from the center-of-mass after excluding the identified opening, and farthest from the identified opening among the one or more next-farthest locations, and to identify the next-farthest locations as one or more additional openings, wherein the processor is configured to iteratively find each of the next-farthest locations by selecting each next-farthest location based on being farthest, among the one or more next-farthest locations, from the identified openings, until finding a pre-set number of locations; and
      identify the location as a known anatomical opening of the organ.

8. The system according to claim 7, wherein the processor is configured to find the location by calculating paths from the center-of-mass to multiple locations on the surface of the volume, and finding a longest path among the multiple paths.

9. The system according to claim 8, wherein the processor is configured to identify the location by including multiple locations on the surface of the volume that are within a predefined distance from the found location as being part of the opening.

10. The system according to claim 8, wherein the processor is configured to calculate the paths by dividing the surface of the volume into a given number of pixels, and calculating a shortest path to each pixel.

11. The system according to claim 7, wherein the processor is configured to calculate a center of mass inside a mapped volume of a cardiac chamber.

12. The system according to claim 7, wherein the processor is further configured to present the one or more found farthest locations to a user.

* * * * *